United States Patent [19]
Dougherty et al.

[11] Patent Number: 6,054,600
[45] Date of Patent: Apr. 25, 2000

[54] NON-TOXIC SOLVENT SOLUBLE GROUP IV AND V METAL ACID SALT COMPLEXES USING POLYETHER ACID ANHYDRIDES

[75] Inventors: T. Kirk Dougherty, Playa Del Rey; John J. Drab, Santa Barbara; O. Glenn Ramer, Los Angeles, all of Calif.

[73] Assignee: Raytheon Company, Lexington, Mass.

[21] Appl. No.: 09/307,589

[22] Filed: May 7, 1999

[51] Int. Cl.[7] ................................. C07F 7/00; C07F 9/00
[52] U.S. Cl. ............................. 556/44; 556/55; 556/105; 556/437; 427/126.3; 423/608; 423/617; 423/618
[58] Field of Search ................................. 556/44, 55, 105, 556/437; 427/126.3; 423/608, 617, 618

[56] References Cited

U.S. PATENT DOCUMENTS

| | | | |
|---|---|---|---|
| 5,410,276 | 4/1995 | Hwang et al. | 330/297 |
| 5,434,102 | 7/1995 | Watanabe et al. | 437/130 |
| 5,439,845 | 8/1995 | Watanabe et al. | 437/130 |
| 5,602,268 | 2/1997 | Fung | 556/57 |
| 5,721,009 | 2/1998 | Dougherty et al. | 427/126.6 |
| 5,885,648 | 3/1999 | Dougherty et al. | 427/8 |

FOREIGN PATENT DOCUMENTS

93/12538  6/1993  WIPO ..................... 21/316

OTHER PUBLICATIONS

J.V. Mantese et al., "Metalorganic Deposition (MOD): A Nonvacuum, Spin–on, Liquid–Based, Thin Film Method", *MRS Bulletin*, pp. 48–53 Oct. 1989.

G.M. Vest et al., "Synthesis of Metallo–Organic Compounds for MOD Powders and Films", *Materials Research Society*, vol. 60, pp. 35–42, (1986).

Callender et al, "Aqueous Synthesis of Water–Soluble Alumoxanes: Enviromentally Benign Precursors to Alumina and Aluminum–Based Ceramics", *Chem. Mater*, vol. 9, pp. 2418–2433, (1977).

Apblett et al., "Metal Organic Precursors for YTTRIA", *Phosphorus, Sulfur, and Silicon*, vol. 93–94, pp. 481–482, (1994).

Bahl et al, "Heavy Alkaline–Earth Poyether Carboxylates", *Inorg. Chem.*, vol. 36, pp. 5413–5415 (1997).

*Primary Examiner*—Porfirio Nazario-Gonzalez
*Attorney, Agent, or Firm*—Colin M. Raufer; Leonard A. Alkov; Glenn H. Lensen, Jr.

[57] ABSTRACT

Novel metal acid salt complexes are provided comprising (1) a metal selected from Group IV and Group V metals and (2) a polyether acid, along with a process for making the salt complexes. The process comprises: (a) preparing a polyether acid anhydride from the corresponding polyether acid; and (b) combining a metal alkoxide containing the Group IV or Group V metal with the polyether acid anhydride to form the metal acid salt complex. The resulting Group IV and Group V metal acid salt complexes enable the production of improved thin film, thick film, and bulk ceramic metal oxides and mixed metal oxides for a number of applications, including ferroelectric, electrooptic, paraelectric, and piezoelectric devices, using liquid soluble precursors which are soluble in far less toxic solvents than in the prior art. The soluble ceramic precursors may also be used as reactive binders and shape-forming aids in conventional ceramic processing.

20 Claims, No Drawings

NON-TOXIC SOLVENT SOLUBLE GROUP IV AND V METAL ACID SALT COMPLEXES USING POLYETHER ACID ANHYDRIDES

TECHNICAL FIELD

The present invention is generally directed to the synthesis of polyether acid anhydrides, useful in the preparation of Group IV and V metal acid salt complexes. More specifically, the present invention is directed to the synthesis of Group IV 3,6-dioxaheptanoates (e.g., Ti and Zr) and Group V 3,6-dioxaheptanoates (e.g., Ta and Nb).

BACKGROUND ART

The anhydride of 3,6-dioxaheptanoic acid has been described in PCT Publication WO-9103542 and Japanese Patent JP 90252800 as useful in formulations of mildew removers containing peroxide per acid materials.

The synthesis of thin film ceramic from metal organic acid salts (most usually aliphatic acids such as neodecanoic or 2-ethylhexanoic) is described in, for example, application Ser. No. 09/300,962, filed Apr. 28, 1999, entitled "Voltage Variable Capacitor or Varactor for High Frequency Power Modulator"; application Ser. No. 08/863,117, filed May 27, 1997, entitled "Process for Making Stoichiometric Mixed Metal Oxide Films"; J. V. Mantese et al, "Metalorganic Deposition (MOD): A Non-vacuum, Spin-on, Liquid-Based, Thin Film Method", *MRS Bulletin*, pp. 48–53 (October 1989); "Process for Fabricating Layered Superlattice Materials", PCT Publication WO 93/12538 (Applicant: Symetrix Corporation); U.S. Pat. No. 5,434,102, entitled "Process for Fabricating Layered Superlattice Materials and Making Electronic Devices Including Same", issued Jul. 18, 1995, to H. Watanabe et al; U.S. Pat. No. 5,439,845, entitled "Process for Fabricating Layered Superlattice Materials and Making Electronic Devices Including Same", issued Aug. 8, 1995, to H. Watanabe et al; and G. M. Vest et al, "Synthesis of Metallo-Organic Compounds for MOD Powders and Films", *Materials Research Society Symposium Proceedings*, Vol. 60 pp. 35–42 (1986).

The use of the anhydride of 2-ethylhexanoic acid to better control the reaction of metal alkoxides to metal salts is disclosed and claimed in U.S. Pat. No. 5,721,009, entitled "Controlled Carbon Content MOD Precursor Materials Using Organic Acid Anhydride", issued Feb. 24, 1998, to T. K. Dougherty et al.

A review of the need for environmentally-benign ceramic precursors and the alumina precursor made from 3,6-dioxaheptanoic acid and an alumina mineral (Group III precursor) is described by R. L. Callendar et al in "Aqueous Synthesis of Water-Soluble Alumoxanes: Environmentally Benign Precursors to Alumina and Alumina Based Ceramics", *Chemical Materials*, Vol. 9, No. 11, pp. 2418–2433 (1997).

A. W. Apblett et al, "Metal Organic Precursors to Yttria", *Phosphorous, Sulfur, and Silicon*, Vol. 93–94, pp. 481–482 (1994) disclose a Group III metal from yttrium acetate and the free acid including 2-ethyhexanoic acid and 3,6-dioxaheptanoic acid.

A. M. Bahl et al, "Heavy Alkaline Earth Polyether Carboxylates", *Inorganic Chemistry*, Vol. 36, No. 23, pp. 5413–5415 (1997) disclose calcium, barium, and strontium with 3,6-dioxaheptanoic acid from the free acid and the metal hydroxides.

In the last three references listed above, the 3,6-dioxaheptanoic acid salts are all made using either aqueous-based chemistry or a reaction in which water is a by-product. This may be the reason why the Group IV and V metal salts do not appear in the prior art. The present inventors show herein that the water causes gelling for these higher valence metals, and anhydrous techniques are therefore needed for these syntheses.

DISCLOSURE OF INVENTION

In accordance with the present invention, the synthesis, reactivity, and use of anhydrides of polyether acids, such as 3,6-dioxaheptanoic acid anhydride, as an intermediate for ceramic oxide precursors are provided. The molecule is most useful for producing the metal acid salts (the acid being 3,6-dioxaheptanoic acid and related polyether acids) of Group IV and V metals. These soluble acid salts are useful as precursors to the Group IV and V ceramic metal oxides and have not been described in the prior art. For example, the titanium (IV) salt of 3,6-dioxaheptanoic acid may be coated onto a substrate and subsequently pyrolyzed to give a thin film of titanium oxide. The acid salts are soluble in common non-toxic polar organic solvents (for example, methanol, ethanol, propanol, methoxy ethanol, and others). In addition, these salts are soluble in water or water/solvent mixtures of the common polar organic solvents. During reduction to practice of this and the related inventions, the inventors have shown that the resulting thin films made from these materials are of higher quality than those from prior art. It should be noted that only the lower valent metal salts of the polyether acids have been described previously in the prior art.

Specifically, in accordance with the present invention, salt complexes are provided comprising a metal selected from Group IV and V metals and a polyether acid.

Further in accordance with the present invention, a process for making the salt complexes is provided. The process comprises:

(a) preparing a polyether acid anhydride from the corresponding polyether acid; and (b) combining a metal alkoxide with the polyether acid anhydride to form the salt complex.

The present invention enables production of improved thin film metal oxide materials using liquid soluble precursors which are soluble in far less toxic solvents than in the prior art. The teachings of the present invention provide for a wider range of possible elements that can be used as compared to the prior art. Finally, the present invention enables the fabrication of improved electronic devices from less toxic and easier handled precursors and solvents.

BEST MODES FOR CARRYING OUT THE INVENTION

The present invention provides for a wider range of precursor materials for ceramic oxide fabrication that provide higher quality films using less toxic materials. In a previous disclosure, application Ser. No. 09/300,962, filed Apr. 28, 1999, a thin film voltage variable capacitor (varactor) is described for use in a patented high frequency power converter (U.S. Pat. No. 5,410,276, entitled "RF Modulation Using a Pulsed DC Power Supply", issued Apr. 25, 1995, to W. B. Hwang et al). In that previous disclosure, a thin film of barium strontium titanate (BST) was made by solution deposition and pyrolysis of a solution of barium, strontium, and titanium 2-ethylhexanoate salts. The solvents used were xylene, n-butyl acetate, and the isopropyl ester of 2-ethylhexananioc acid. Although giving good voltage tunability of the capacitor, the devices thus formed had unacceptable leakage currents and had too low a Q for the desired application. Further, xylene and n-butyl acetate are considered to be toxic and thus undesirable for use in device formation.

Although the metal salts of barium and strontium are easily made by reaction of the free acid with the appropriate metal as described in the related disclosure, the production of the titanium salt of 3,6-dioxaheptanoic acid is more problematic. The inventors, and others, have previously reacted 2-ethylhexanoic acid or anhydride with titanium (IV) iso-propoxide to form the soluble Ti(IV)-2-ethylhexanoate. However, use of the free acid of 3,6-dioxaheptanoic acid in this reaction invariably forms gels (no doubt due to the higher reactivity and solubility of water in this acid). As such, the use of the anhydride method (which is the basis for the present invention) allows for production of a broader range of elements of metal salts of 3,6-dioxaheptanoic acid (and other polyether acids) as previously demonstrated in the prior art. Thin films made from these materials give improved electrical properties, and the precursors are compatible and processed with much less toxic solvents.

In the same manner, U.S. Pat. No. 5,885,648, entitled "Process for Making Stoichiometric Mixed Metal Oxide Films" and issued Mar. 23, 1999, to T. K. Dougherty et al and U.S. Pat. No. 5,721,009, supra, describe improved ferroelectric thin film materials useful for microelectronic memory applications. In those disclosures, the material deposited is a mixture of the 2-ethyl hexanoate salts of bismuth, strontium, tantalum, and niobium to give the bismuth-layered ferroelectric strontium bismuth tantalum niobate (SBTN; $SrBi_2Ta_{2-x}$—$Nb_xO_9$, where x is 0–2). Again, the polyether acid salts of tantalum and niobium have not been disclosed in the prior art. Upon attempt to make this material using an acid alkoxide interchange method, gelling occurred. It was found necessary to use the anhydride of the acid to give a soluble polyether acid precursor for these Group V elements.

The patented VHF power converter (U.S. Pat. No. 5,410,276, supra) was developed to meet the demanding cost and performance requirements of high power, high frequency electronic systems such as active arrays and high speed processors. The use of the ferroelectric (FE) variable capacitor to regulate the power converter greatly decreases the circuit complexity cost, weight and will improve device system performance. The patented FE memory allows replacement of the 20+ pound, archaic plated wire memory in, e.g., missile guidance systems, with 32 memory chips. As such, the present invention provides for improved and less toxic materials useful for manufacture of these (and other) products.

In a broader sense, the present invention allows production of improved metal oxide precursor for ceramics and metal oxide thin films. It extends the use of the polyether acids (one example being 3,6-dioxaheptanoic acid) as precursor salts to the Group IV and V metal oxides. Other examples of polyether acids include 3,6,9-trioxaheptanoic acid, methoxy acetic acid, and ethoxy acetic acid. Essentially, the polyether acids useful in the practice of the present invention are polyethers of ethylene glycol, having the formula $$CH_3O(CH_2CH_2O)_nCH_2COOH$$

where n is 0 to 2.

The use of polyether acids for the formation of Group IV and V metal oxides has not been previously shown in the prior art. The ceramic precursors disclosed herein are soluble in more common and much less toxic solvents than the prior art.

Summarizing, improved thin film materials have made using the metal salts of 3,6-dioxaheptanoic acid (and more broadly, other polyether acids) as compared to the all aliphatic acid analogues (for example, 2-ethylhexanoic acid or neodecanoic acid). These precursors are soluble and can be processed using much less toxic solvents. However, the prior art only describes the complexes and forming of Group II and III metal oxides and precursors. The prior art describes the precursors of the Group II metals (barium, calcium, and strontium) with 3,6-dioxaheptanoic acid and other polyether acid analogues. The prior art also describes the production of two (yttrium and aluminum) Group III metal acid salts of 3,6-dioxaheptanoic acid and analogues. Work completed for the present invention and related disclosures show that Group IV and V metal salts of the polyether acids may not be made by these prior described routes. These are best made using the anhydride of the polyether acid and reaction of that with the appropriate metal alkoxides. The prior art uses methods which produce water which forms gels in reactions of the intermediates of the higher valence metals.

The general synthetic route to providing Group IV and V polyether acid anhydride metal acid salt complexes is as follows:

1. Prepare polyether acid anhydride from corresponding polyether acid by combining the polyether acid with a dehydrating agent; and
2. Prepare metal acid salt complex by combining, in the case of Group IV metal, a mixture of the polyether acid and the polyether acid anhydride and metal alkoxide, either simultaneously or sequentially, or, in the case of Group V metal, only the polyether acid anhydride and metal alkoxide. Alternatively, in the case of Group IV metal, the polyether acid anhydride and metal alkoxide may be reacted directly, without the polyether acid.

The dehydrating agent used in the first reaction may comprise any of the known dehydrating agents used to convert organic acids to the corresponding anhydride. Examples include dicyclohexylcarbodiimide and acetic anhydride.

The temperature of the first reaction tends to be mildly exothermic, and is preferably maintained at or near room temperature.

The metal alkoxide used in the second reaction may comprise any of the known Group IV or V alkoxides. Group IV alkoxides include metals selected from the group consisting of titanium, zirconium, silicon, lead, and hafnium. Group V alkoxides include metals selected from the group consisting of tantalum, niobium, and vanadium. Preferably, tantalum, niobium, and titanium alkoxides are employed in the practice of the present invention.

The alkoxides are given by the general formula $$(R-O)_m-Me$$

where R is substituted and unsubstituted straight or branched alkyls ($C_1$ to $C_8$) and aryls, Me is a Group IV or V metal, and m is an integer of 4 (for Group IV metals) or 5 (for Group V metals).

The temperature used in the second reaction is elevated, typically between about 40° and 120° C., and preferably at or near the higher end of the range.

In the case of Group IV metals, the ratio of anhydride to acid in the second step above is in the range of about 25:75 to 100:0 anhydride:acid.

The following details the synthesis of three metal polyether acid complexes useful as precursors for metal oxides. The materials are soluble in non-toxic solvents.

Synthesis of 3,6-Dioxaheptanoic Acid Anhydride

Into a dry nitrogen-purged, 1 L three-necked, round-bottom flask attached with addition funnel and mechanical stirrer apparatus was placed dicyclohexylcarbodiimide (142.5 gram, 0.69 mol) dissolved in a toluene/hexane mixture (300 mL toluene and 100 mL hexane). The addition funnel was charged with 3,6-dioxaheptanoic acid (182 gram, 1.35 mol). The acid was added to the dehydrating agent over a period of 2 hours. The reaction contents were kept near room temperature by placing the reactor in a ice-cooled water bath. Following addition, the contents of the reaction mixture were stirred overnight. The next day, the solid urea by-product was separated from the desired product by vacuum filtration and the solid washed with hexane/toluene and the combined filtrates and washings concentrated in vacuum on a rotary evaporator. The resulting mobile liquid was purified by distillation at high vacuum to give the product 3,6-dioxaheptanoic acid anhydride (b.p. 110°–115° C. at 0.05 mm of Hg; 142 grams at 84% yield; $^1$H NMR (CDCl$_3$): 4.31 (brd s, 2H), 3.72 (m, 2H), 3.56 (m, 2H), 3.35 (m, 3H); $^{13}$C NMR (CDCl$_3$): 58.53, 68.42, 70.59, 71.51, 165.85. The C-NMR shows the product to be contaminated with small amounts of the free acid and the urea by-product.

Attempted Synthesis of Titanium (IV) 3,6-Dioxaheptanoate From Titanium Iso-Propoxide and 3,6-Dioxaheptanoic Acid This reaction was attempted several times, with gelling occurring on each effort. As the reaction proceeds, there is a build-up of propanol in the flask. When significant quantities of alcohol and acid are present, the two combine (perhaps catalyzed by the metal center) to give ester and water. The water then hydrolyzes and crosslinks the remaining metal alkoxides to give a useless gel. Attempts to remove the ethanol by distillation and reduce the contact of acid and alcohol by partial addition of the acid did not lead to significant improvement. One of these reactions is described below:

Into a dry nitrogen-purged, 100 mL, round-bottom flask was placed titanium iso-propoxide (15 gram, 0.053 mol) and 3,6-dioxaheptanoic acid (21.3 gram 0.159 mol, 3 equivalents). A small exotherm was observed. A short path distillation unit was attached and the contents heated in a 120° C. oil bath. Immediately, an amount of liquid was removed and collected by distillation. The liquid was shown to be 2-propanol (7.6 gram, 0.127 mol, 2.4 equivalents). Another quantity of the acid was added (14.0 gram, 0.104 mol, 2 equivalents) and the reaction was again heated to 120° C. Although a amount of alcohol was further removed at this stage, the contents of the reaction flask soon became very viscous and finally gelled. This product was, of course, useless for solution deposition work.

Synthesis of Titanium (IV) 3,6-Dioxaheptanoate From Titanium Iso-Propoxide and 3,6-Dioxaheptanoic Acid and 3,6-Dioxaheptanoic Acid Anhydride The idea in this synthesis is to prevent the gelling of the intermediate metal complex by preventing water and crosslinking by removing the alcohol in the early stages of the reaction and using the anhydride to complete exchange of the alkoxides in the final stages of the reaction. This method has been shown to give water and air stable and useful precursor liquids and avoids the extra step to remove the ester by-product as was necessary in the case for the Group V (Ta and Nb) examples, infra:

Into a dry nitrogen-purged, 100 mL, round-bottom flask was placed titanium iso-propoxide (12.12 gram, 0.0426 mol) and 3,6-dioxaheptanoic acid (14.57 gram, 0.108 mol, 2.5 equivalents). A short path distillation unit was attached and the contents heated in a 120° C. oil bath. Immediately, an amount of liquid was removed and collected by distillation. This was determined to be 2-propanol (5.6 gram, 0.0.093 mol). The mixture was cooled and 3,6-dioxaheptanoic acid anhydride (8.4 gram, 0.037 mol) was added and the reaction heated at 120° C. for 2 hours. NMR analysis of the reaction showed the exchange of the acid with the alkoxides to be complete. The resulting yellow mobile liquid was soluble in the common polar organic solvents and water (total mass 24.67 gram, 8.26% Ti). A small amount of this liquid was concentrated to give a solvent/volatile-free viscous liquid for NMR analysis (the volatiles were determined to be 2-propanol and 3,6-dioxaheptanoic acid 2-propyl ester). $^1$H NMR (CDCl$_3$): 4.2 (brd s, 2H), 3.5 (m 2H), 3.35 (m, 2H), 3.20 (m, 3H); $^{13}$C NMR (CDCl$_3$): 58.37, 68.25, 70.15, 71.38, 169.45. This precursor liquid may be used to make BST thin films, such as described in related application Ser. No. 09/300,962.

Synthesis of Tantalum (V) 3,6-Dioxaheptanoate From Tantalum Ethoxide and 3,6-Dioxaheptanoic Acid Anhydride The Group V metals were much more prone to crosslinking/gelling as compared to Group IV metal titanium. The anhydride technique was used exclusively for these samples. This necessitated the removal of the by-product ester to give a solution with a sufficient amount of ceramic solids to be useful.

Into a dry nitrogen-purged, 100 mL, round-bottom flask was placed tantalum ethoxide (15 gram, 0.037 mol) and 3,6-dioxaheptanoic acid anhydride (46.23 gram, 0.18 mol, 5.0 equivalents). The reaction was heated to 120° C. using an external oil bath and the progress of the reaction was followed by $^1$H NMR spectroscopy. The exchange was complete after two hours. The contents of the flask were cooled and the materials concentrated to remove a large quantity of the by-product 3,6-dioxaheptanoic acid ethyl ester. The resulting yellow mobile liquid was soluble in the common polar organic solvents (total mass 35.2 gram, 19.0% tantalum). A small amount of this liquid was further concentrated to give a solvent/volatile-free viscous liquid for NMR analysis. $^1$H NMR (CDCl$_3$): 4.1 (brd s, 2H), 3.5 (m, 2H), 3.35 (m, 2H), 3.20 (m, 3H); $^{13}$C NMR (CDCl$_3$): 58.56, 68.29, 70.36, 71.52, 170.06. This precursor liquid may be used to make SBTN thin films as described in U.S. Pat. No. 5,885,648.

Synthesis of Niobium (V) 3,6-Dioxaheptanoate From Niobium Ethoxide and 3,6-Dioxaheptanoic Acid Anhydride This material was made analogously as the tantalum example, supra. This precursor liquid may be used to make SBTN thin films as described in U.S. Pat. No. 5,885,648.

INDUSTRIAL APPLICABILITY

The polyether anhydrides and the resulting Group IV and V metal acid salt complexes are expected to find use in the formation of thin films, thick films, and bulk ceramics of a variety of mixed metal oxides for a number of different applications, including ferroelectric, electrooptic, paraelectric, photoferroelectric, and piezoelectric devices, to name a few.

Thus, there has been described a process for forming a polyether anhydride and its use in the formation of Group IV and V metal acid salt complexes. It will be readily apparent to those skilled in this art that various changes and modifications of an obvious nature may be made, and all such changes and modifications are considered to fall within the scope of the appended claims.

What is claimed is:

1. A metal acid salt complex comprising (1) a metal selected from the group consisting of Group IV and Group V metals and (2) a polyether acid.

2. The metal acid salt complex of claim 1 wherein said Group IV metal is selected from the group consisting of titanium, zirconium, silicon, lead, and hafnium.

3. The metal acid salt complex of claim 1 wherein said Group V metal is selected from the group consisting of tantalum, niobium, and vanadium.

4. The metal acid salt complex of claim 1 wherein said polyether acid is given by the formula $$CH_3O(CH_2CH_2O)_nCH_2COOH$$

where n is 0 to 2.

5. A method of preparing a metal acid salt complex, said method comprising combining (1) a metal alkoxide containing a metal selected from the group consisting of Group IV and Group V metals and (2) a polyether acid anhydride.

6. The method of claim 5 wherein said Group IV metal is selected from the group consisting of titanium, zirconium, silicon, lead, and hafnium.

7. The method of claim 5 wherein said Group V metal is selected from the group consisting of tantalum, niobium, and vanadium.

8. The method of claim 5 wherein said polyether acid is given by the formula $$CH_3O(CH_2CH_2O)_nCH_2COOH$$

where n is 0 to 2.

9. A process for preparing a metal acid salt complex comprising (1) a metal selected from the group consisting of Group IV and Group V metals and (2) a polyether acid anhydride, said process comprising:

(a) preparing said polyether acid anhydride from its corresponding polyether acid; and (b) combining a metal alkoxide containing said metal with said polyether acid anhydride to form said salt complex.

10. The process of claim 9 in which said metal alkoxide is a Group IV metal alkoxide.

11. The process of claim 10 wherein said Group IV metal is selected from the group consisting of titanium, zirconium, silicon, lead, and hafnium.

12. The process of claim 11 wherein said metal alkoxide is given by the formula $$(R-O)_4-Me$$

where R is substituted and unsubstituted straight or branched alkyls ($C_1$ to $C_8$) and aryls and Me is said Group IV metal.

13. The process of claim 10 comprising reacting said metal alkoxide with a mixture of said polyether acid and said polyether acid anhydride, either simultaneously or sequentially.

14. The process of claim 13 wherein both said reacting steps are carried out at an elevated temperature in the range of 40° to 120° C.

15. The process of claim 13 wherein said polyether acid anhydride and said polyether acid are employed in a ratio of anhydride to acid in a range of about 25:75 to 100:0 anhydride:acid.

16. The process of claim 9 wherein said metal alkoxide is a Group V metal alkoxide.

17. The process of claim 16 wherein said Group V metal is selected from the group consisting of tantalum, niobium, and vanadium.

18. The process of claim 16 wherein said alkoxide is given by the formula $$(R-O)_5-Me$$

where R is substituted and unsubstituted straight or branched alkyls ($C_1$ to $C_8$) and aryls and Me is said Group V metal.

19. The process of claim 16 wherein said combining step is carried out at an elevated temperature in the range of 40° to 120° C.

20. The process of claim 9 wherein said polyether acid anhydride is given by the formula $$CH_3O(CH_2CH_2O)_nCH_2COOH$$

where n is 0 to 2.

* * * * *